(12) United States Patent
Liu et al.

(10) Patent No.: US 8,124,415 B2
(45) Date of Patent: Feb. 28, 2012

(54) METHOD AND TEST FOR BLOOD SERUM COMPONENT ANALYSIS

(75) Inventors: Kan-Zhi Liu, Winnipeg (CA); Anthony Shaw, Winnipeg (CA)

(73) Assignee: National Research Council of Canada, Ottawa, ON (CA)

( * ) Notice: Subject to any disclaimer, the term of this patent is extended or adjusted under 35 U.S.C. 154(b) by 426 days.

(21) Appl. No.: 12/000,334

(22) Filed: Dec. 11, 2007

(65) Prior Publication Data

US 2008/0153171 A1    Jun. 26, 2008

Related U.S. Application Data

(60) Provisional application No. 60/874,677, filed on Dec. 14, 2006.

(51) Int. Cl.
*G01N 33/92* (2006.01)
*G01N 31/00* (2006.01)

(52) U.S. Cl. .................. 436/71; 702/1; 702/22; 702/23; 702/25

(58) Field of Classification Search ............ 436/71; 702/1, 22, 23, 25
See application file for complete search history.

(56) References Cited

U.S. PATENT DOCUMENTS 7,022,527 B2   4/2006  Liu et al.
(Continued)

OTHER PUBLICATIONS

Petibois et al., Plasma Protein Contents Determined by Fourier-Transform Infrared Spectroscometry, Clinical Chemistry, 2001, 47:4, pp. 730-738.*

(Continued)

*Primary Examiner* — Christine T Mui
(74) *Attorney, Agent, or Firm* — Jason Davis

(57) ABSTRACT

The discovery that apolipoprotein B exhibits spectral features in the mid IR spectrum that make it identifiable within blood serum leads to the invented use of a statistical correlation between a concentration of apolipoprotein-B (apoB) in a sample of blood serum and infrared spectral features of the blood serum sample to produce a test for apoB. A method for providing such a test, and tests produced by the method are taught.

17 Claims, 7 Drawing Sheets

U.S. PATENT DOCUMENTS

2004/0248309 A1* 12/2004 Liu et al. .................... 436/71

OTHER PUBLICATIONS

Manning M.C., "Use of infrared spectroscopy to monitor protein structure and stability", Expert Reviews in Proteomics, 2005, 5, p. 731-743.

Van De Weert et al:, "Fourier Transform Infrared Spectrometric Analysis of Protein Conformation . . . ", Analytical Biochemistry, 2001, 297, p. 160-169.

Li et al., "Comparison of performance of partial least squares regression . . . ", Analytical and Bioanalytical Chemistry, 2007, 387, p. 603-611.

Sato et al., "Application of Fourier-transform infrared (FT-IR) spectroscopy for simple and easy . . . ", Clinica Chimica Acta, 2010, 411, p. 285-290.

Johnson et al., "Tietz Fundamentals of clinical chemistry", Tietz Textbook of Clinical Chemistry, 1996, 3, p. 477 and 481, W.B. Saunders Co.

Benezzeddine-Boussaidi et al., "Validation for quantification of immunoglobulins by Fourier transform infrared spectrometry", Clin. Chem. Lab. Med., 2009, vol. 47, p. 83-90.

Heise et al., "Multicomponent Assay for Blood Substrates in Human Plasma by Mid-infrared Spectroscopy . . . ", Appl. Spectrosc., 1994, vol. 48, p. 85-95.

Massart et al., "Selectivity and Specificity", Chemometrics: A Textbook, 1988, ch. 8, p. 115-126, Elsevier Books.

Petibois et al., "Determination of Glucose in Dried Serum Samples by Fourier-Transform Infrared Spectroscopy", Clinical Chemistry, 1999, vol. 45, p. 1530-1535.

Petibois et al., "Glucose and lactate concentration determination on single microsamples by Fourier-transform . . . ", J. Lab. Clin. Med., 2000, vol. 135, p. 210-215.

Petibois et al., "Plasma Protein Contents Determined by Fourier-Transform Infrared Spectrometry", Clinical Chemistry, 2001, vol. 47, p. 730-738.

Shaw et al., "Multianalyte Serum Analysis using Mid-infrared Spectroscopy", Ann. Clin. Biochem., 1998, vol. 35, p. 624-632.

Smith, B., "Chemometric Methods and Factor Analysis", Quantitative Spectroscopy: Theory and Practice, 2003, p. 125-179.

Ward et al., "Postprandial blood glucose determination by quantitative mid-infrared spectroscopy", Appl Spectrosc., 1992, vol. 46, p. 959-965.

Liu, Kan-Zhi et al, "Apolipoprotein B Quantification by Infrared Spectroscopy", Spec 2006 proceedings—Jun. 27, 2006.

Fuster V., et al, "Matching the Intensity of Risk Factor Management . . . " J Am Coll Cardiol 27:964-976, 1996.

Sniderman A.D., et al "Errors that result from using the TC/HDL C ratio rather than . . . "J Intern Med 259:455-461 (2006).

Walldius, G. et al; "The apoB/apoA-I ration is better than the cholesterol . . . " Clin Chem Lab Med 42:1355-1363 (2004).

Barter P.J. et al; "Apo B versus cholesterol in estimating cardiovascular . . . " J. Intern Med 259:247-258 (2006).

Sniderman A.D., et al; "Concordance/discordance between plasma apolipoprotein B levels . . . " Am J. Cardiol 91: 1173-1177 (2003).

Sniderman A.D., et al; "Apolipoproteins versus lipids as indices of coronary . . . "Lancet 361:777-780 (2003).

Sniderman A.D., et al; "Counterpoint: to (measure apo) B or not . . . "Clin Chem 43:1310-1314 (1997).

Sniderman A.D. et al; "The measurement of apolipoprotein B should replace the conventional . . . " Can J Cardio. 8:133-138 (1992).

Walldius G., et al; The apoB/apoA-I ration: a strong, new risk factor for cardiovascular . . . J Intern Med 259:493-519 (2006).

Gotto A.M. Jr., et al; "Relation between baseline and on-treatment lipid parameters and first acute coronary events . . . "; Circulation 101:477-484 (2000).

Rosseneu M. , et al "Some considerations of methodology and standardization of . . . " Clin Chem. 29: 427-433 (1983).

Pruvot I., et al "Electroimmunoassay for determination of ApoB in human sera by using . . . " Clin Chem 33:1070 (1987).

Cano M.D., et al "Measurement of apolipoproteins B and A by radial immunodiffusion: . . . " Ann Biol Clin 52:657-661 (1994) Paris.

Bedford D.K. et al "Radioimmunoassay for human plasma apolipoprotein B" Clin Chim Acta 70:267-276 (1976).

Curry M.D. et al "Electroimmunoassay, radioimmunoassay, and radial immunodiffusion assay evaluated . . . " Clin Chem 24:280-286 (1976).

Durrington P.N. et al "A comparison of methods for the immunoassay of serum apolipoprotein . . . " Clin Chim Acta 71: 95-108 (1976).

James R.W. et al "A non-competitive enzyme-linked immunosorbent assay for measuring human-plasma . . . " Clin Chim Acta 151:3173-24 (1985).

Ballantyne F.C. et al "estimation of apolipoprotein B in man by immunoephelometry" Clin Chem 24:788-792 (1976).

Hallaway B.J. et al "Apolipoprotein B quantified by particle-concentration fluorescence immunoassay" Clin Chem 38: 2387-2391 ((1992).

Riepponen P., et al "Immunoturbidimetric determination of apolipoproteins A-1 and B . . . " Scan J. Clin Lab Invest. 47:739-44 (1987).

Shaw R.A. et al "Multianalyte serum analysis using mid-infrared spectroscopy" Ann Clin Biochem 35:624-632 (1998).

Liu K.Z. et al "Reagent-free, simultaneous determination of serum cholesterol in HDL . . . " Clin Chem 48:499-506 ((2002).

Scanu A., et al "On the conformational instability of human serum low-density lipoprotein: effect of . . . " Proc Nat Acad Scien 62:171-178 (1969).

Herzyk E. et al "Changes in the secondary structure of apolipoprotein B-100 after . . . " Biochim Biophys Acta 922: 145-154 (1987).

Goormaghtigh E., et al "Evaluation of the secondary structure of apo B-100 in low-density lipoprotein . . . " Biochim Biophys Acta 1006:147-150 (1989).

Goormaghtigh E., et al "Secondary structure of the particle associating domain of apolipoprotein B-100 . . . " Biochemistry 32: 6104-6110 (1993).

Elden W., "Partial least squares vs. lanczos bidiagonalization-I: analysis of a projection method for . . . " Computational Statistics & Data Analysis, 46:11-31 (2004).

Cader F., et al "Infrared quantitative analysis" Encyc. Anall. Chem. pp. 10879-10909 (2000).

Hasegawa T.,"Principal components regression and partial least squares modeling" Handbook of Vibrational Spectroscopy pp. 2293-2312 (2002).

Surewicz W.K. et al; Determination of protein secondary structure by Fourier transform infrared . . . Biochemistry 32:389-94 (1993).

* cited by examiner

METHOD AND TEST FOR BLOOD SERUM COMPONENT ANALYSIS

CROSS-REFERENCE TO RELATED APPLICATION

This application claims the benefit of U.S. provisional application No. 60/874,677, filed Dec. 14, 2006, the entire content of which is hereby incorporated by reference.

FIELD OF THE INVENTION

This invention pertains in general to the field of blood analysis, and, in particular, to the spectroscopic analysis of serum components.

BACKGROUND OF THE INVENTION

Cardiovascular disease remains a leading cause of death in North America and Western Europe, with atherosclerosis being the principal cause. It has long been recognized that cholesterol plays a role in the formation of atherosclerotic plaques. The encouraging news, however, is that there are very effective interventions for those at risk of cardiovascular disease. Accordingly, the central challenge is to identify those who are at risk. Of all the factors that are commonly measured to gauge elevated risk, the single most effective indicator is serum low density lipoprotein (LDL) ("bad") cholesterol. As good as this test is, however, there is now overwhelming evidence that a better alternative exists, namely serum apolipoprotein-B (apoB).

Cholesterol circulates in the bloodstream within complex, multi-component lipoprotein particles. These are further subdivided into very low density (VLDL), low density (LDL), intermediate density (IDL) and high density lipoproteins (HDL). Each LDL, IDL, and VLDL particle is comprised of a single apolipoprotein B molecule, as well as cholesterol, triglycerides, and cholesterol esters. Cholesterol may be imagined as a passenger on a LDL ship. It is now becoming increasingly more evident that the risk of cardiovascular disease is better represented by a number of "ships" (serum LDL particle concentration) than by a number of "passengers" on them (serum LDL cholesterol concentration). As demonstrated, for example, by Walldius G, et. al. (2004), the apoB/apoA-I ratio is better than the cholesterol ratios to estimate the balance between plasma proatherogenic and antiatherogenic lipoproteins and to predict coronary risk (Clinical Chemistry and Laboratory Medicine. 42:1355-1363, and Sniderman A D (1992). It has therefore been recommended that the measurement of apolipoprotein B should replace the conventional lipid profile in screening for cardiovascular risk. Canadian Journal of Cardiology 8:133-138. ApoB remains associated with the LDL, IDL or VLDL particle from the time of its assembly, through its secretion, and metabolic transformation within the circulation, and ultimately to its catabolism.

Total apoB concentration in serum includes LDL, IDL, VLDL, chylomicrons, and lipoprotein(a) particles, and therefore represents an estimate of the total atherogenic particle count. LDL makes up the vast majority of these (Walldius G, et al. Clin Chem Lab Med 42:1355-1363). ApoB has proven superior to LDL cholesterol in gauging risk of cardiovascular disease. Most importantly, the difference in predictive accuracy is most pronounced (in favour of apoB) for those populations most at risk, e.g. elderly males.

The treatment most often prescribed for people at elevated CAD risk is statin therapy, which has the effect of lowering serum LDL cholesterol levels. Recent clinical evidence has shown that here, again, apoB is a better gauge of treatment efficacy. For patients on statin treatment, apoB proved to be a better predictor of outcome than LDL cholesterol, as demonstrated by, Sniderman A D, et al. (2003), Apolipoproteins versus lipids as indices of coronary risk and as targets for statin treatment (Lancet 361:777-780). This research indicates that if statin therapy were guided by targeting desirable serum apoB levels rather than their LDL cholesterol counterparts, statins would reduce the rate of clinical events significantly below that presently achieved.

The potential demand for apoB testing is clear, either as an adjunct to, or replacement for, conventional lipid testing.

While there are numerous ways that apoB can be detected according to the prior art (e.g. electroimmunoassay, radial immunodiffusion, radioimmunoassay enzyme-linked immuno-sorbent assays, nephelometric assays and turbidimetric assays), each of these methods has their own drawbacks that are known in the art. None of these methods has proven easy and cost effective to automate for mass screening. Some of the drawbacks include the requirement for a large volume of antisera, inherent disadvantages of the use of radioactivity, and matrix effect problems (i.e. problems with interferences caused by other components in the serum).

Applicants have previously obtained U.S. Pat. No. 7,022,527, the entire contents of which are incorporated herein by reference, which teaches that a set of clinically relevant serum analytes may be determined accurately based on mid-infrared spectroscopy of serum, including total cholesterol, HDL cholesterol, triglycerides, and LDL cholesterol. Advantageously, this method does not use antisera, and has proven reliable, and cost effective. Naturally a method that analyses sera optically is relatively unconstrained, as the test can be applied on a sample whenever a spectrometer and processor time are available. In contrast, the above-identified methods require other fluids to control or react with the blood serum. These other fluids have shelf-lives and require procedures that are more time consuming, expensive, and difficult to automate.

IR spectroscopy has been applied previously in research studies of lipoprotein structures. For instance, Scanu et al. have employed IR spectroscopy to examine the thermal behavior of apoB (Scanu et al., 1969, PNAS 62: 171-178). IR has also been used to elucidate the secondary structure of apoIB, first qualitatively using resolution-enhancement techniques (Herzyk et al., 1987, Biochim Biophys Acta 922: 145-154) and then quantitatively using curve fitting of deconvolved spectra (Goormaghtigh et al., 1989, Biochim Biophys Acta 1006: 147-150). More recently, Goormaghtigh et al have utilized IR spectroscopy to reveal the structure of the lipid attached proteins that remain following proteolytic digestion of solvent-exposed regions (Goormaghtigh et al., 1993, Biochemistry 32: 6104-6110).

It has been demonstrated previously that IR spectroscopy may be used to quantify several serum analytes, including glucose, urea, triglycerides, total protein, albumin, total cholesterol, LDL cholesterol, and HDL cholesterol. Some of these compounds occur in the highest concentrations in human serum. Indeed, a relatively high concentration and a distinctive infrared absorption spectrum, are both prerequisite to quantification by infrared spectroscopy. The root-mean-square (RMS) error of analyte quantification is typically about 0.1 g/L for the IR spectroscopy-based assays in comparison with accepted clinical analytical counterparts.

Nonetheless, IR spectroscopy cannot be reliably used to detect many serum analytes, for example, because they are present in such low concentrations that they do not contribute meaningfully to the infrared spectrum, or because the mid-infrared absorption pattern closely resembles that of one or more components of similar or higher concentration. An example of the first would be any analyte for which absorptions lie below the noise level of the measurement; so since the RMS error is typically 0.1 g/L for target analytes with favorable spectroscopic absorption profiles, this clearly precludes the meaningful quantification of any analyte (such as serum creatinine and uric acid) with typical concentrations below 0.1 g/L, as RMS error would be larger than the measured concentration. An example of the latter occurs when existing spectroscopic features of the analyte are masked by the absorptions of one or more other components. Under this condition, the RMS error for the target assay would be expected to rise above the benchmark level of 0.1 g/L.

The list of known analytes that cannot be assayed by IR spectroscopy is a long one. It will be appreciated by those skilled in the art that blood serum is an extraordinarily complex mixture, and carries many different components (blood proteins, inorganic electrolytes, glucose, lipids, amino acids, hormones, metabolic end products, carbon dioxide, oxygen, etc.) in concentrations that vary from species to species, from individual to individual, and over time within an individual, for example depending on the health of the individual. As described above, in order to reliably quantify a serum analyte for a target group of individuals, that analyte must provide a set of identifying spectral features that are strong enough to contribute to the measured serum spectrum and are not interfered with by the other components. Because these characteristics may not be known a priori, it is not always known a priori whether a specific serum analyte can be reliably quantified by IR spectroscopy.

The core apolipoproteins within high density and low density lipoprotein particles, apoA-I and apoB, constitute examples of target serum analytes that would not be expected to be amenable to infrared spectroscopy-based quantitative analysis. Both of these compounds typically fall in the concentration range 0.5-1.5 g/L.

The applicants have not found techniques, for example, to produce a test for apoA-I concentration that is satisfactorily reliable, despite the fact that the concentration range for this protein is typically 0.5-1.5 g/L. Although this concentration range lies above the 0.1 g/L uncertainty level typical of glucose, urea, and cholesterol, the attempt to develop an IR-based assay failed. This failure may be caused by the absorption profile of apoA-I being dwarfed by the strong absorptions of serum albumin and globulins, which constitute the major circulating serum proteins. At typical total concentrations of about 70 g/L, the absorption patterns arising from these proteins are 50-70 times stronger than the absorptions contributed by apoA-I. Because the structural elements of proteins are very similar for different proteins, their absorption profiles may only be distinguished under extraordinary circumstances. The expectation, borne out by the experience in attempting the apoA-I assay, is that the absorptions of proteins in blood serum will be masked by the much stronger, superimposed absorption profiles of serum proteins present in larger concentrations (albumin and globulins), and that the overall similarities among these profiles will work in concert to preclude the development of IR-based assays for other proteins.

A reliable, low cost blood serum test for apoB is highly desirable, especially one that could be readily automated.

SUMMARY OF THE INVENTION

Applicants have discovered that apoB can be reliably detected using mid-infrared spectroscopy of serum.

According to an aspect of the invention, a statistical correlation between a concentration of apoliprotein-B (apoB) in blood serum and infrared spectral features of the blood serum is used to produce a test for apoB.

According to another aspect of the invention a method is provided for producing a test for apoB concentration. The method involves obtaining a mid infrared spectral representation for each blood serum sample from a set of standard blood serum samples that are statistically representative of a target group, each blood serum sample having a known concentration of apolipoprotein-B (apoB); computing a statistical correlation between the known concentrations of apoB and intensities of spectral features manifest in respective spectral representations to identify a set of spectral features correlated with apoB concentration within the set of standard samples; and using the correlated spectral features to define a test that can be applied to test spectral representations of test blood serum samples from the target group to determine a quantity of apoB in the test blood serum.

The computation of the statistical correlation may involve applying a partial least squares analysis of the spectral representations and known concentrations of apoB, and using the correlated spectral features may involve defining a regression coefficient vector.

Obtaining the mid infrared spectral representations for each of the set of samples may involve obtaining the sera, and drying the samples to produce respective films. The mid infrared spectral representations may be 9 point Savitzky-Golay smoothed second derivative absorption spectra of the samples.

The method may further involve applying the test to a test blood serum sample to determine the concentration of apoB in the test blood serum sample.

Further aspects of the invention are provided in terms of tests produced by the method above. As will be appreciated by those of skill in the art, the test may include an operator that is applied to a test spectral representation and an argument, such as the regression coefficient vector if the PLS algorithm is used for computing the statistical correlation. The test may be encoded on computer readable program instructions, and may be associated with instructions for obtaining the test spectral representation of the test sample. Preferably these instructions effectively reproduce the method of obtaining the mid infrared spectral representations for the blood serum samples from the set to minimize systematic error. The computer readable program instructions may comprise program instructions for implementing the test of the test spectral representation, or may comprise program instructions for producing the test spectral representation from collected light from the test blood serum sample. The test may further be associated with a spectrometer used for collecting the infrared light.

Mid IR-spectroscopic based approaches to analysis and quantitation have several attractive features. They require no reagents, they are linear over the entire physiological concentration range, and they are well suited for automation. In the context of Applicant's U.S. Pat. No. 7,022,527, it is worth noting that the same measurement can yield not only serum apoB levels, but also the four serum constituents (total cholesterol, HDL cholesterol, triglycerides, and LDL cholesterol) that make up a lipid panel.

Further features of the invention will be described or will become apparent in the course of the following detailed description.

BRIEF DESCRIPTION OF THE DRAWINGS

A better understanding of the invention and its objects will be had with regard to the Detailed Description below in conjunction with the attached drawings in which.

DETAILED DESCRIPTION OF PREFERRED EMBODIMENTS

The invention provides a method for determining a concentration of apolipoprotein-B (apoB) in a blood serum using IR spectroscopic imaging of serum.

Unless defined otherwise, all technical and scientific terms used herein have the same meaning as commonly understood by one of ordinary skill in the art. Although any methods and materials similar or equivalent to those described herein can be used in the practice or testing of the present invention, the preferred methods and materials are now described.

As used herein, "serum" or "serum sample" refers to the clear liquid part of the blood that remains after blood cells and clotting proteins have been removed. Serum differs from plasma primarily in its lack of coagulation factors. It can be simply obtained by drawing blood into a test tube without anticoagulation reagents, centrifuging to remove cells, and allowing the plasma supernatant to clot. Filtration methods are also available for extracting serum from a blood sample.

Figure 1:
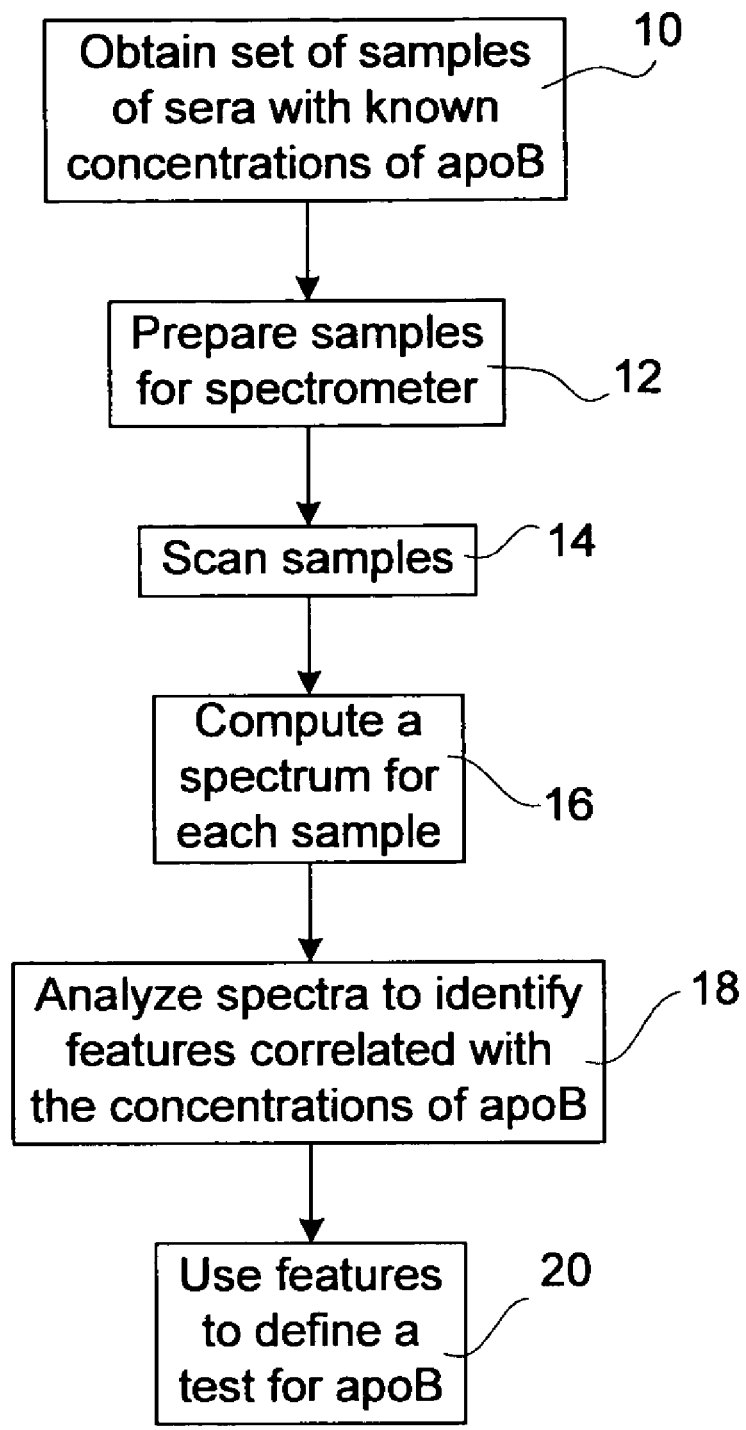
FIG. 1 is a flow chart illustrating principal steps involved in a method for obtaining a test for apoB concentration in blood serum, in accordance with an embodiment of the invention.

FIG. 1 is a flow chart illustrating the principal steps involved in obtaining a test for concentration of apoB in blood serum. In step 10, a set of blood serum samples are obtained. The set is chosen as a statistically representative set of samples from among a population or target group of individuals for which the test is designed. Each sample is associated with a known apoB concentration, which may be determined by any other known method for apoB concentration determination. An uncertainty of the apoB concentrations of the samples is a significant bound on the accuracy of the constructed quantitation test.

In step 12, the samples are prepared for spectral analysis. While there are different possible methods available for this, applicants have found that there are benefits associated with drying small volumes (a few microliters) of the samples, for example, by exposure to ambient conditions for a brief period, causing the sample to form a film when water content is removed. The use of a dry film has advantages over measuring spectra of the aqueous samples: this procedure avoids the inconvenience and imprecision involved in working at very short pathlengths that are required for transmission spectroscopy of native serum, eliminates the spectral interference of water absorptions that may otherwise obscure certain spectral features of the solute(s) of interest, and can provide inherently better spectral resolution by virtue of eliminating water/solute interactions.

In step 14, the samples are scanned by a spectrometer, e.g. a Fourier transform infrared spectrometer (FT-IR). The scanning involves detecting and analyzing the profile of intensity vs. wavelength (or, equivalently and more commonly the "wavenumber", which is the inverse of the wavelength in centimeters) of mid IR radiation that has been attenuated upon passage through the sample. An absorption spectrum "$A(v)$" is produced when the incident radiation spectrum "$I_0(v)$" is compared with the spectrum of IR radiation as attenuated by the sample, "$I(v)$", according to $A(v)=-\log(I(v)/I_0(v))$. In some embodiments, in particular, those making use of FT-IR spectrometers, higher quality spectra are obtained by averaging a plurality of scans in a conventional manner. It is well known in the art to make use of a number of different mathematical filters, smoothing functions, and like noise reducing transforms to, raw data from a spectrometer.

In general, the more closely the processing of the spectra for test samples mirrors the processing of the spectra for samples within the training set, the more accurate the test procedure, as consistent handling of raw spectral data will lead in turn to a consistent basis for comparison of the spectral features. The same spectral preprocessing steps were used for the training and test sets to establish the optimal analytical algorithm, and accordingly it is known that by mirroring the preprocessing steps employed in deriving that algorithm, it can be applied to new spectra/samples.

The spectrometer outputs signals used to produce mid IR spectral representations of the respective samples in step 16. While steps 10-16 are steps for providing mid IR spectral representations, it will be appreciated by those of skill in the art that other methods for providing a set of mid IR spectral representations can be provided in other ways, and where such alternative methods produce equally or more accurate spectral representations and concentrations of apoB in the corresponding samples, an equally accurate or more accurate test for apoB concentration may be produced.

In steps 18 and 20 the information about all samples in the set, i.e. a mid IR spectral representation and the apoB concentration, is analyzed collectively with statistical analysis software to determine spectral features that are correlated with the apoB concentration. Applicants have determined mid IR absorption spectral features using a partial least squares (PLS) analysis method known in the art. Now that it is known that the information is manifest in the mid IR absorption spectra, other statistical analysis methods could be used to obtain a formally different set of spectral features. It will be appreciated that each different sample set will provide slightly different spectral features, and different kinds of spectral features may be obtained by different kinds of statistical analysis methods.

For example, principal component regression or multiple wavelength linear regression, might also be contemplated to the same end. Indeed, it has been appreciated for some time that partial least squares, principal component regression (PCR), and multiple wavelength linear regression methods all provide equivalent or nearly equivalent accuracy in the quantification of a given target compound by infrared spectroscopy (Eldén, 2004; Cadet and de la Guardia, 2000; Hasegawa, 2002). PLS and PCR can be used as regularized solutions to undersampled multiple regression problems. PLS carries out supervised principal components analysis automatically, taking into account a target vector (Eldén, 2004). Therefore, in practice, PLS typically yields a more parsimonious solution than the traditional PCR, where the principal components (PCs) are chosen in an unsupervised way. However, when the PCs used in PCR co-vary strongly with the target vector (the concentrations for the analyte of interest), the performances of PCR and PLS are comparable.

The output of the analysis may itself include a specification of one or more spectral features, or may be used to produce a representation of the spectral features in the form of an argument for a test. For example, a difference, product, division, or other two place operation of the argument with a suitable mid IR spectral representation of a test sample yields a number that strongly corresponds to the apoB content of the test sample. The argument and operator form a test as the term is used herein. If the statistical analysis is PLS, the operator is vector multiplication, and the argument is a regression coefficient vector.

It will be appreciated by those of skill in the art that mathematical operations and transforms can easily be applied to the test argument, for example, so that the argument can be applied by an operation to a test sample that is treated differently than the samples of the set, to produce a different kind of spectral representation of the test sample than the kind of spectral representation of the sample from the set.

It will further be appreciated that the test, and/or an argument therefor may be encoded in a carrier signal and be computer readable, for example, to permit delivery of the test. The test may be incorporated in whole or in part, in a software application or other program instructions. As such the test may be applied by a general purpose computer. Alternatively the test may be included in an article comprising the program instructions and a spectroscope with onboard spectrum analysis capabilities.

Figure 2:
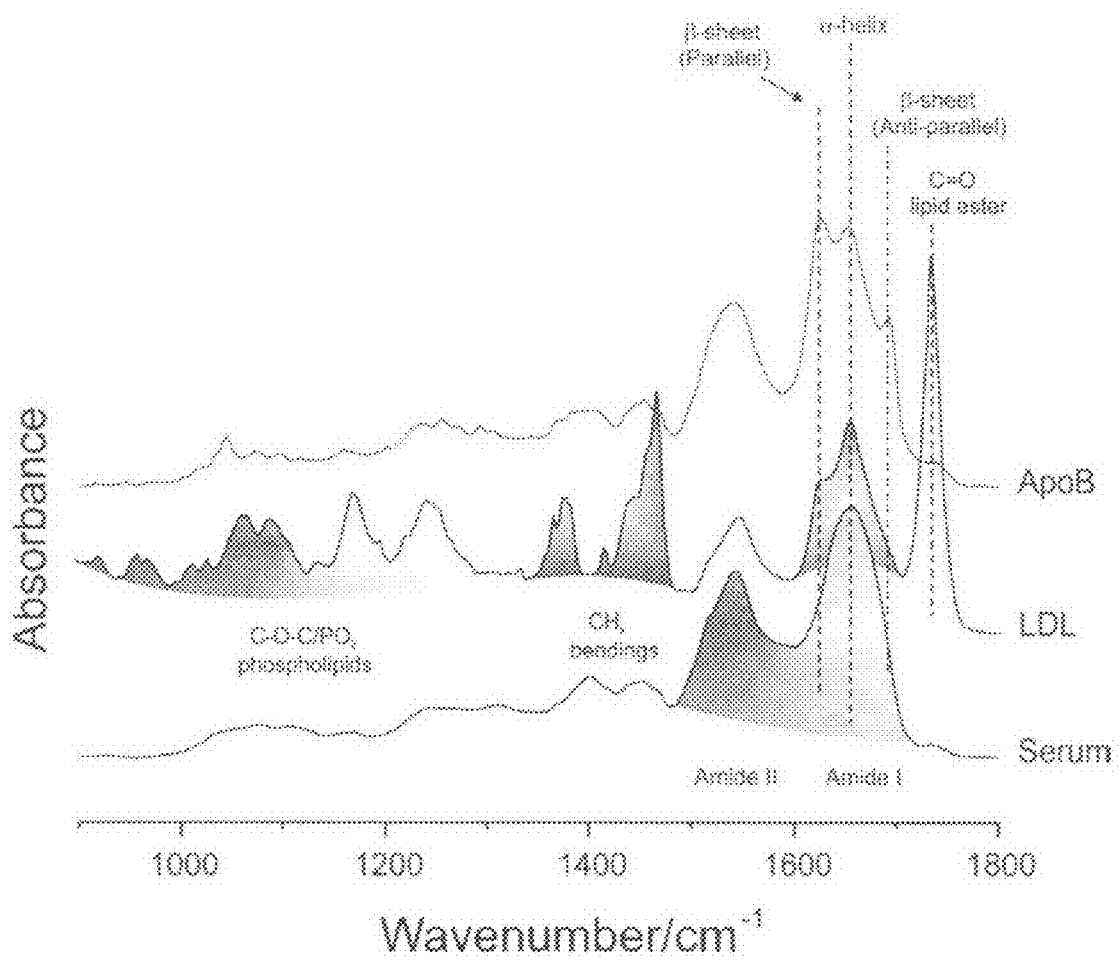
FIG. 2 is a typical infrared absorption spectrum for a serum film, overlaid by spectra for dried LDL, and apoB films.

FIG. 2 schematically illustrates a typical infrared absorption spectrum for a serum film, overlaid by the normalized spectra of dried LDL and apoB.

The spectrum of LDL reveals strong peaks in the amide II band (primarily a NH bending vibration) centered at ~1550 cm$^{-1}$, and in the amide I band (C=O stretch) at ~1650 cm$^{-1}$. The lipid acyl chains and terminal $CH_3$ groups give rise to bands at 1467 and 1378 cm$^{-1}$ respectively, while bands at 1242 and 1088 cm$^{-1}$ correspond to the two $PO_2^-$ stretching vibrations of the phospholipid groups. Ester C—O—C asymmetric and symmetric stretching vibrations (1173 and 1065 cm$^{-1}$, respectively) of phospholipids, triglycerides and cholesteryl esters dominate the spectral region to lower wavenumber, while the ester C=O stretch contributes the strongest absorption of all, at 1738 cm$^{-1}$.

Since apoB is the only protein within LDL particles, it is of particular interest to compare the infrared spectra of LDL and apoB with a representative spectrum of dry serum film within the 1500-1700 cm$^{-1}$ region, which is a wavenumber region dominated by bands originating with the protein amide groups. The profile of the amide I band complex is quite different for LDL compared to its serum counterpart, in particular showing a clear shoulder at 1620 cm$^{-1}$ which usually reflects β-sheet structure.

This was further confirmed by looking at the apoB spectrum as shown in FIG. 2, that the three strongest subcomponents are assigned to β-structure and α-helical domains, respectively. This is consistent with a previous IR spectroscopy study, which assigned ~40% β-sheet structure of LDL to apoB (Goormaghtigh E, et al, 1989). The high percentage of β-sheet structure was suggested to substantiate the importance of such segments in maintaining the lipid-protein assembly in LDL.

EXAMPLES

Materials:

A total of 366 anonymized human serum samples, collected in serum separator tubes, (Becton Dickinson Vacutainer Systems, Franklin Lakes, N.J.) were obtained from the Winnipeg Health Science Centre clinical chemistry laboratory. The corresponding apoB concentrations were determined in the same laboratory by an immunoturbidimetric method, and provided together with the samples. Standard LDL was obtained from Sigma-Aldrich Corp., St. Louis, Mo.

Methods:

Samples were prepared for spectroscopic measurements by drying duplicate 2 μl serum aliquots under ambient conditions onto a silicon wafer divided into 96 circular wells (each of 5 mm diameter) by an adhesive plastic mask. Infrared spectra of such films were recorded with a Bruker Vector 22 spectrometer (Bruker Optics, Billerica, Mass.) equipped with a HTS (High Throughput Sampling) accessory and a home-built wafer mount. The HTS accessory allows for the automated sequential acquisition of spectra for 95 films (and one blank well, used for the background measurement) distributed on the silicon wafer. Spectra were acquired at a nominal resolution of 4 cm$^{-1}$. Each sample and a background measurement were scanned 256 times to produce an average, high signal to noise ratio spectrum. The absorbance spectra were further processed as required for partial least squares (PLS) calibration model development and validation.

PLS Regression Analysis:

Because serum is a complex multi-component fluid, no single absorption or set of absorptions can be identified to quantify analytes present in small quantities such as apoB in serum. Multivariate analysis approaches can be used to identify and quantify analytes from a complex multi-component fluid. PLS is a well known analysis technique for absorbance spectra analysis. The PLS quantification algorithm was developed by splitting the 366 samples into a training set and test set, with 246 samples (492 spectra) and 120 samples (240 spectra), respectively. Trial PLS calibrations and spectral manipulations (mean centering and Savitzky-Golay derivatives) were carried out using GRAMS/32 and PLSplus/IQ software packages (Thermo Electron, Waltham, Mass. 02454).

Results:

Several PLS trials were executed with various choices of spectral region(s), and different preprocessing options (e.g. using 1st derivative, or 2nd derivative of the acquired spectra). A standard error of cross-validation is used as a gauge of relative accuracy for the trials. Representative trials are summarized in Table 1.

TABLE 1

Summary of representative PLS trials.

| Wavenumber range (cm$^{-1}$)[a] | # of derivative smoothing points[b] | SECV(g/L)[c] (15 factors) |
|---|---|---|
| 800-1500, 1700-1800, 2800-3500 | 7 | 0.163 |
| 1500-1700 | 7 | 0.151 |
| 800-1800, 2800-3500 | 7 | 0.136 |
| 800-1800, 2800-3500[d] | 7 | 0.147 |
| 800-1800, 2800-3500 | 9 | 0.134 |
| 800-1800, 2800-3500 | 11 | 0.137 |
| 800-1800, 2800-3500 | 15 | 0.142 |
| 800-1800, 2800-3500 | 19 | 0.142 |
| 800-1800 | 7 | 0.140 |
| 800-1800 | 9 | 0.138 |
| 800-1800 | 11 | 0.141 |
| 800-1800 | 15 | 0.145 |
| 800-1800 | 19 | 0.145 |
| 1100-1800, 2800-3500 | 7 | 0.136 |
| 800-1100, 1400-1800, 2800-3500 | 7 | 0.139 |

TABLE 1-continued

Summary of representative PLS trials.

| Wavenumber range (cm$^{-1}$)$^a$ | # of derivative smoothing points$^b$ | SECV(g/L)$^c$ (15 factors) |
|---|---|---|
| 800-1400, 2800-3500 | 7 | 0.175 |
| 1400-1800, 2800-3500 | 7 | 0.140 |
| 1400-1800 | 7 | 0.144 |

$^a$Wavenumber range for PLS trial.
$^b$All trials illustrated are for Savitzky-Golay smoothed second derivative spectra. This column shows the number of points used for the Savitzky-Golay smoothing.
Note:
All trials with other choice of derivative or no derivative preprocessing were inferior to their $2^{nd}$ derivative counterparts.
$^c$Standard error of cross-validation for the training set.
$^d$Spectra not normalized to a common intensity over the region 800-1800 cm$^{-1}$.
(Note:
This procedure was carried out for all other trials listed here.)

The best results obtained a calibration model for analyzing sera that uses a $2^{nd}$ derivative of the acquired spectra, to which 9-point Savitzky-Golay smoothing is applied. Spectral regions encompassing the 1100-1800 and 2800-3500 cm$^{-1}$ wavenumbers were found to have the highest accuracies. The trial subjected to 9-point Savitzky-Golay smoothing second derivative spectral representations of the wavenumber regions 800-1800, 2800-3500 cm$^{-1}$ were chosen for further analysis. It is this trial that is referred to hereinbelow as the selected trial.

Figure 3:
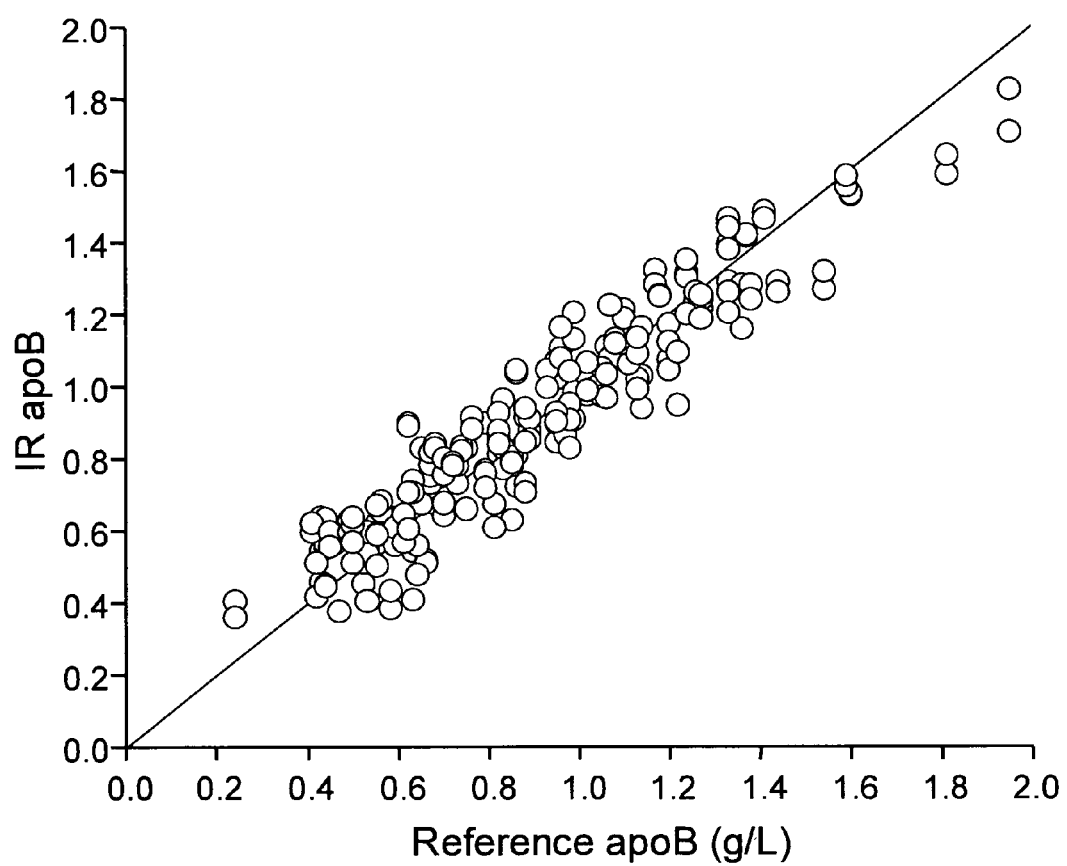
FIG. 3 is a graphical comparison of apoB levels as determined in accordance with a method of the invention with counterpart values as provided by an accepted clinical laboratory method.

FIG. 3 is a scatterplot comparing IR-predicted apoB concentration to reference apoB concentration associated with the respective samples (determined with the immunoturbidic assay method), for the 120 samples of the test set, using the selected trial. The 15-factor model, built with the training set of spectra subjected to these preprocessing parameters and spectral regions, provided a standard error of cross-validation of 0.134 g/L and predicted the test set samples with a standard error of 0.10 g/L, with a regression coefficient of r=0.94.

Figure 4:
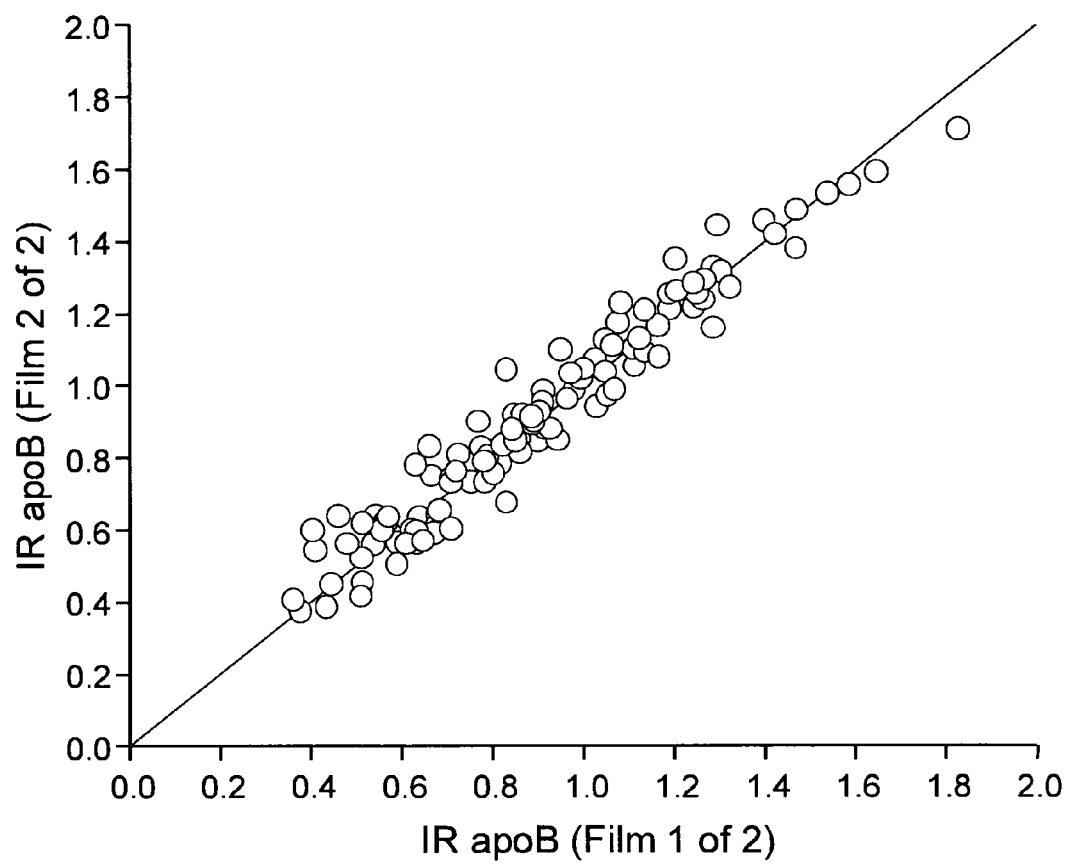
FIG. 4 is a graphical comparison of apoB levels as determined in duplicate for several serum specimens, in accordance with a repetition of a method of the invention.

FIG. 4 is a scatterplot comparing IR-predicted apoB concentrations of paired films that were derived from the same serum aliquots. A precision/reproducibility of the IR-based quantification method is determined by the comparison. The standard deviation of duplicate measurements was calculated to be 0.05 g/L.

The relative uncertainty attributable to film choice as compared with all other error factors combined was estimated by the equation $\sigma_{other}^2 = \sigma_{total}^2 - \sigma_{film\ choice}^2$, where the total error is assessed relative to the concentration of apoB associated with the serum aliquot (i.e. 0.10 g/L). The conclusion is that the uncertainty contributed by the film choice plays a relatively minor role ($\sigma_{film\ choice}$=0.05 g/L) in comparison with all other factors combined ($\sigma_{other}$=0.09 g/L).

The IR-based assay shows very good correlation with the reference (immunoturbidimetric) assay used to calibrate and test it (FIG. 3), and further shows good precision in replicate measurements (FIG. 4).

Figure 5:
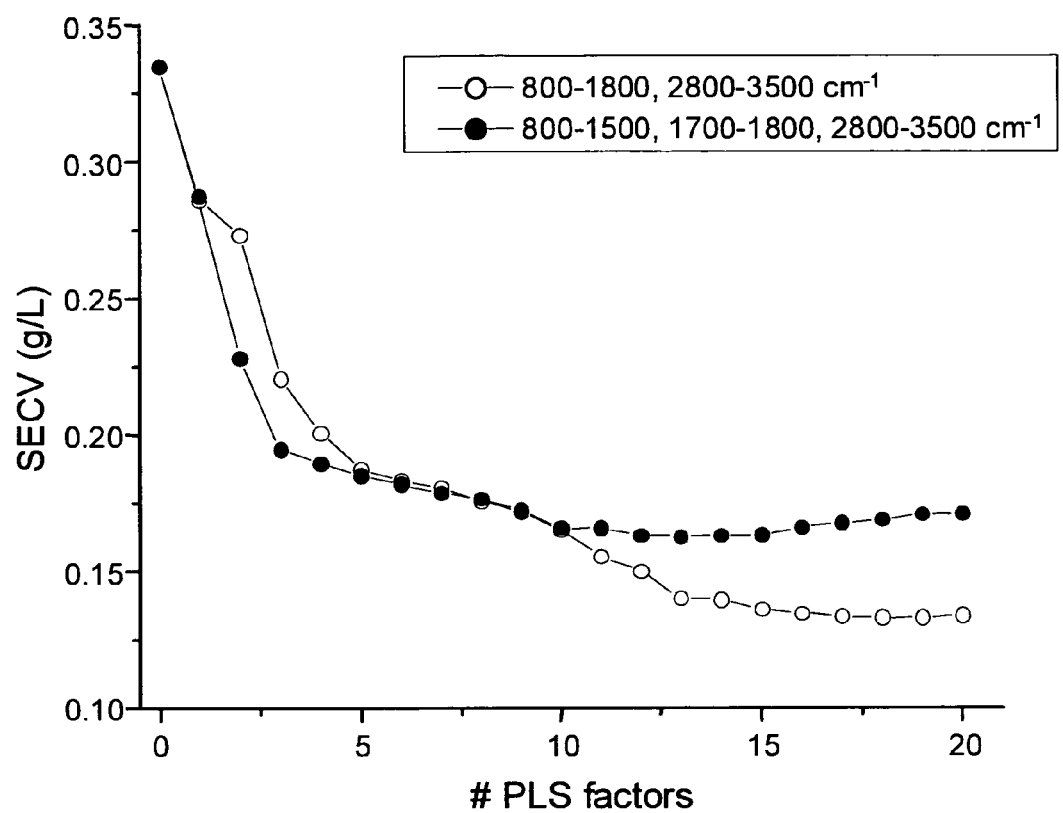
FIG. 5 is a graphical representation of the standard error of cross-validation (SECV) as a function of a number of factors for PLS computational models using different mid-IR ranges.

FIG. 5 is a graph plotting the standard error of cross-validation vs. number of factors for two PLS models that illustrate the important role of the apoB protein absorptions in quantifying serum apoB. A first note is that the general shape of both plots is highly desirable in that the SECV decreases rapidly for the first 10 factors, and then levels off. As such it will be evident that a substantially optimal regression coefficient vector (or like test argument) can be produced with a relatively small number of regression coefficients.

One of the two trials shown in FIG. 5 is the selected trial. The other is identical in all ways except that the region 1500-1700 cm$^{-1}$ was excluded. For PLS models up to and including 10 factors, the two are very similar. Most striking is the divergence between the two plots starting with the addition of the $11^{th}$ factor and continuing thereafter. This divergence shows a significant drop in the accuracy of the test when the 1500-1700 cm$^{-1}$ wavenumber region is excluded.

Figure 6:
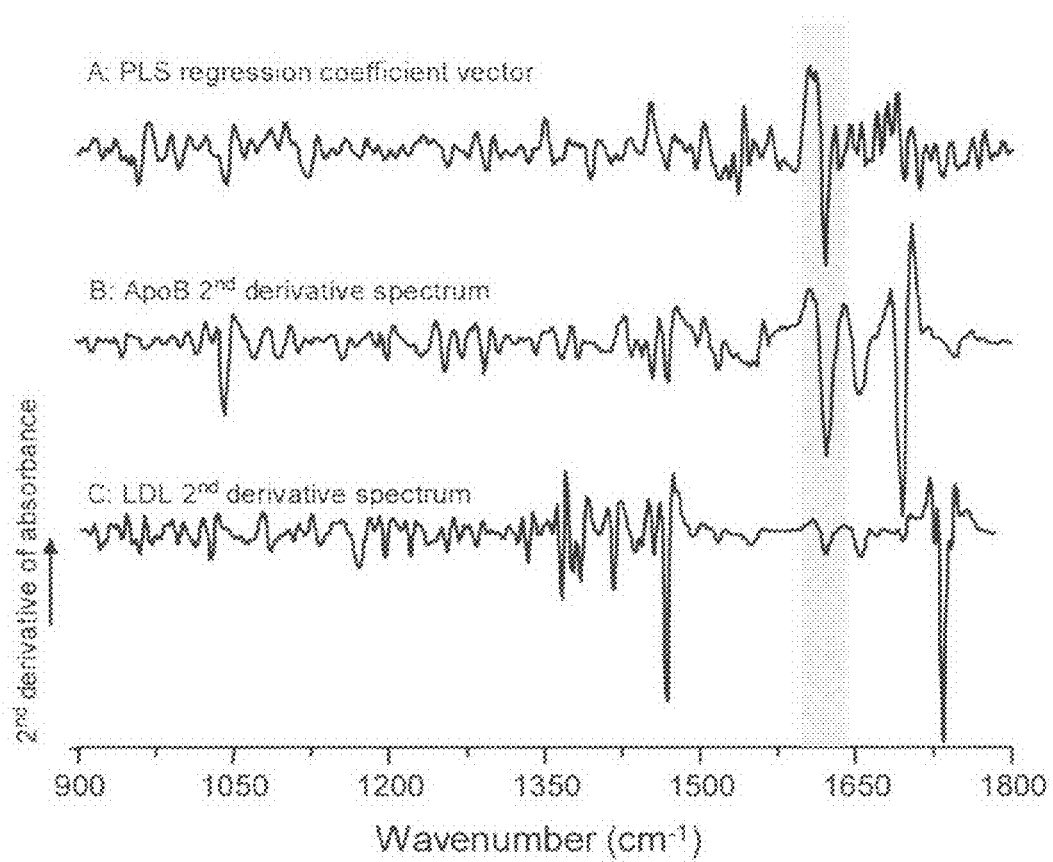
FIG. 6 is a graphical representation of the PLS regression coefficient vector, with the second derivative spectra of LDL and apoB films also plotted for comparison; and, FIG. 7 is a graphical representation of each of the fifteen factors of the regression coefficient vector shown in FIG. 6.

FIG. 6 compares the $2^{nd}$ derivative spectra of LDL and apoB to the optimal PLS regression coefficient vector. Features contributing to the success of the 15 factor PLS model of the selected trial are highlighted by comparing the PLS regression coefficient vector (A) to the $2^{nd}$ derivative spectra for the dried apoB (B) and LDL (C) films (spectra are offset along the vertical axis for clarity). The 1600-1700 cm$^{-1}$ region was found particularly useful to optimize the accuracy of the PLS model; the comparison highlighted here reveals that the largest PLS regression coefficients coincide with the 1620 cm$^{-1}$ absorption of apoB.

Figure 7:
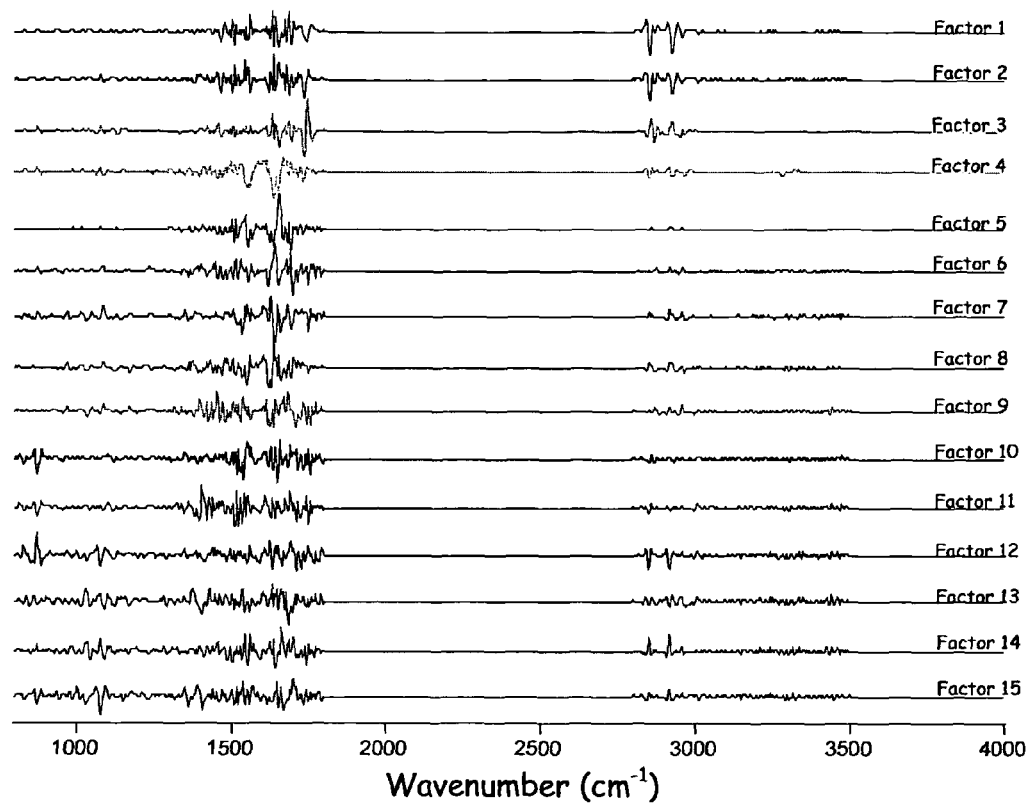

FIG. 7 is a graphical representation of the fifteen factors of the PLS regression coefficient vector A shown in FIG. 6. Recurrence of the same wavenumber regions in each factor emphasizes the importance of these wavenumber regions.

While not wanting to be limited by the following theory, applicants postulate that the explanation for the accuracy of the IR-based apoB assay, in contrast with the failure of the apoA-I assay, may lie in the difference in a secondary structure of apoB as compared to apoA-I. ApoB has a distinctive secondary structure that has a stability conferred onto it by its binding within the LDL particle, which appears to contribute substantially to the overall accuracy of the apoB assay.

It is well known that the absorption positions of many IR spectroscopic features of proteins are sensitive to protein conformation (e.g. Surewicz et al, 1993). Particularly useful are the amide I absorptions in the range 1600-1700 cm$^{-1}$, that correspond to stretching vibrations of the backbone carbonyl groups. It has been observed empirically that the major structural motifs, α-helix and β-sheet, give rise to distinct absorptions at ~1655 cm$^{-1}$ and 1640 cm$^{-1}$ respectively. This is relevant to a key feature illustrated within FIG. 2, namely the fact that apoB contributes an absorption at 1624 cm$^{-1}$. This band is attributed to the β-sheet structural elements of apoB, as is the absorption at 1695 cm$^{-1}$, while the feature at 1654 cm$^{-1}$ denotes α-helical domains. Less well characterized are the absorption positions for other backbone vibrations, e.g. the amide II and amide III bands that fall in the ranges 1510-1550 and 1240-1300 cm$^{-1}$ respectively, but it is considered that these absorption positions—in particular the amide II bands—are conformationally sensitive. The only reason that they are neglected in conformational studies is that the amide I absorption is always better resolved and less prone to overlap by other absorptions that might lead to spectral misassignments and hence misinterpretation. Difficulty with traditional spectroscopic interpretation does not, however, detract from the fundamental reality that the amide II and amide III absorption patterns are sensitive to protein conformation. Therefore, by virtue of this fact, the spectrum of apoB is fundamentally altered as compared to the spectra of proteins that are predominantly α-helical.

The practical consequence of the β-sheet conformation adopted by apoB is that this structural motif triggers the appearance of a set of characteristic IR absorptions that are believed to serve as the basis for accurate quantification of apoB. If so, features that arise solely as a consequence of the characteristic secondary structure of apoB may be exploited for the quantification of apoB. The finding that these features are distinctive and pronounced enough to provide the basis for apoB quantification is a surprising result.

Evidence that successful apoB quantification is improved by the nature of the apoB secondary structure is found in the form of I) a specific feature within the PLS regression coefficient vector, and II) comparison of PLS quantification models that include the amide I and amide II absorptions to counterpart models that do not. FIG. 6 serves to illustrate the first point: the largest feature in the PLS regression vector is coincident with the apoB absorption at 1624 cm$^{-1}$—the feature most distinctly characteristic of the β-sheet structure. The second point is illustrated by FIG. 5, which demonstrates the contribution of the 1500-1700 cm$^{-1}$ region to the accuracy of the PLS quantification algorithm.

Table 2 provides a characterization of various spectral regions as applied to the PLS quantification of apoB. The spectrum used was partitioned into a plurality of subregions, the majority of which are only 100 cm$^{-1}$ wide. Table 2 summarizes these trials, all of which were produced using the identical (normalized 7-point smoothed Savitzky-Golay 2$^{nd}$ derivative spectra). The aim of this exercise was not to discover a new algorithm more accurate than the selected trial in Table 1, but simply to provide some insight into the distribution of spectral features relevant to apoB quantification. To that end, the standard errors of cross-validation were tabulated for 15-factor models, and are listed in order of decreasing analytical accuracy (increasing SECV). Also listed are the spectroscopic features that are believed to contribute to the efficacy of the most accurate models.

Most striking is that the 1600-1700 cm$^{-1}$ region is among the most accurate of all eleven regions explored. This finding provides evidence that apoB absorptions contribute to the success of this assay, and—in conjunction with the arguments presented above—shows that the 1624 cm$^{-1}$ amide I band emblematic of the apoB β-sheet conformation plays a part in the accurate quantification of apoB.

Other conformationally sensitive apoB absorptions undoubtedly contribute to the accuracy observed for other spectral segments, including the amide III bands in the 1200-1300 cm$^{-1}$ region (possibly extending into the 1300-1400 cm$^{-1}$ region) and skeletal vibrations in the 1000-1100 cm$^{-1}$ region.

Finally, it is recognized that the PLS-based quantification of apoB by IR spectroscopy will also incorporate spectroscopic contributions from components whose concentrations are correlated with that of apoB. This is undoubtedly true of LDL cholesterol and triglycerides, and for that reason it is not surprising to find that the spectroscopic regions 1700-1800 and 1400-1500 cm$^{-1}$ provide the basis for two of the four most accurate PLS trials in Table 2; these regions incorporate the triglyceride/cholesterol C=O stretches and CH$_2$ bending vibrations. However these subregions cannot, either alone or in combination, provide the basis for quantification as accurate as that achieved when regions encompassing absorptions of the apoB protein are included in the PLS model. The lipid/cholesterol absorptions serve only to refine the accuracy that is achieved on the basis of the conformationally sensitive protein bands.

TABLE 2

Summary of illustrative PLS trials

| Wavenumber range (cm$^{-1}$)[a] | SECV (g/L) (15 factors) | Absorptions[b] |
|---|---|---|
| 1600-1700 | 0.178 | ApoB amide I |
| 2800-3000 | 0.178 | Lipid and protein CH stretch |
| 1700-1800 | 0.187 | Lipid/cholesterol C=O stretch |
| 1000-1100 | 0.191 | ApoB skeletal stretch |
| 1400-1500 | 0.200 | Lipid/cholesterol CH$_2$ bend |
| 1300-1400 | 0.203 | (ApoB amide III) |
| 1200-1300 | 0.207 | ApoB amide III |
| 900-1000 | 0.215 | |
| 3000-3500 | 0.221 | |
| 1100-1200 | 0.221 | |
| 800-900 | 0.262 | |
| 1500-1600 | 0.283 | |

[a] Wavenumber range for PLS trial
[b] Absorptions within the corresponding wavenumber range that would be expected to contribute to the accuracy of a PLS apoB quantification method.

REFERENCES

Walldius G. Jungner I, Aastveit A H, Holme I, Furberg C D, Sniderman A D. The apoB/apoA-I ratio is better than the cholesterol ratios to estimate the balance between plasma proatherogenic and antiatherogenic lipoproteins and to predict coronary risk. Clin Chem Lab Med. 2004, 42:1355-1363.

Sniderman A D. The measurement of apolipoprotein B should replace the conventional lipid profile in screening for cardiovascular risk. Can J Cardiol, 1992, 8:133-138.

Sniderman A D, Furberg C D, Keech A, Roeters van Lennep J E, Frohlich J, Jungner I, Walldius G Apolipoproteins versus lipids as indices of coronary risk and as targets for statin treatment. Lancet, 2003, 361:777-780.

Scanu A, Pollard H, Hirz R, Kothary K. On The Conformational Instability of Human Serum Low-Density Lipoprotein: Effect of Temperature—Proceedings of the National Academy of Sciences, 1969, 62: 171-178.

Herzyk E, Lee D C, Dunn R C, Bruckdorfer K R, Chapman D. Changes in the secondary structure of apolipoprotein B-100 after Cu$^{2+}$-catalysed oxidation of human low-density lipoproteins monitored by Fourier transform infrared spectroscopy. Biochim Biophys Acta 1987; 922:145-154.

Goormaghtigh E, De-Meutter J, Van Ioo B, Brasseur R, Rosseneu M, Ruysschaert J M. Evaluation of the secondary structure of apo B-100 in low-density lipoprotein (LDL) by infrared spectroscopy. Biochim Biophys Acta 1989; 1006: 147-150.

Goormaghtigh E, Cabiaux V, De-Meutter J, Rosseneu M, Ruysschaert J M. Secondary structure of the particle associating domain of apolipoprotein B-100 in low-density lipoprotein by attenuated total reflection infrared spectroscopy. Biochemistry 1993; 32:6104-6110. Elden W. Partial least squares vs. Lanczos bidiagonalization-I: analysis of a projection method for multiple regression. Computational Statistics & Data Analysis, 2004, 46: 11-31.

Cader F, De la Guardia M. "Infrared quantitative analysis". In Encyclopedia of Analytical Chemistry. R. A. Mayers, Ed., pp. 10879-10909, John Wiley & Sons Ltd, Chichester, 2000.

Hasegawa T. "Principal component regression and partial least squares modeling" In Handbook of Vibrational Spectroscopy. J. M. Chalmers and P. R. Griffiths, Eds., pp. 2293-2312, John Wiley & Sons, Sussex, 2002.

Surewicz W K, Mantsch H H, Chapman D. Determination of protein secondary structure by Fourier transform infrared spectroscopy: a critical assessment. Biochemistry. 1993, 32; 389-94.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method comprising:
   obtaining a mid infrared spectral representation for each blood serum sample from a set of standard blood serum samples that are statistically representative of a target group, each blood serum sample having a known concentration of apolipoprotein-B (apoB);
   computing a statistical correlation between the known concentrations of apoB and intensities of spectral features manifest in respective spectral representations by supervised or unsupervised multivariate statistical analysis to identify a set of spectral features correlated with apoB concentration within the set of standard samples without making use of a pure apoB spectrum in the analysis; and
   using the correlated spectral features to define a test that can be applied to a test spectral representation of a test blood serum sample from a member of the target group to determine a quantity of apoB in the test blood serum sample the test comprising computer readable program instructions encoding an operation applicable to the test spectral representation to yield a number that corresponds to the apoB content of the test blood serum sample, wherein the test makes no use of the pure apoB spectrum.

2. The method of claim 1 wherein:
   computing the statistical correlation comprises applying a partial least squares analysis to the spectral representations and known concentrations of apoB; and
   using the correlated spectral features comprises defining a regression coefficient vector.

3. The method of claim 1 wherein computing a statistical correlation comprises applying a principal component regression to the spectral representations and known concentrations of apoB.

4. The method of claim 1 wherein obtaining a spectral representation for each blood serum sample comprises obtaining the set of samples having the known concentrations of apoB, and for each blood serum sample:
   subjecting the sample to infrared light; and
   detecting the infrared light in at least one spectral region after interaction with the sample, and producing a signal representing the detected infrared light for producing the spectral representation of the sample.

5. The method of claim 4 wherein obtaining the set of samples comprises obtaining the sera, and drying the samples to produce respective films.

6. The method of claim 4 wherein collecting the infrared light comprises scanning the sample over at least one infrared region a plurality of times, and averaging the scans to produce a high signal-to-noise ratio spectrum.

7. The method of claim 4 wherein producing the spectral representation comprises filtering and mean centering the signal.

8. The method of claim 4 wherein producing the spectral representation comprises applying a 9 point Savitzky-Golay derivative to the signal.

9. The method of claim 4 wherein producing the spectral representation comprises producing a second derivative of the signal.

10. The method of claim 1 further comprising applying the test to the test spectral representation to determine the quantity of apoB in the test blood serum sample.

11. A test for blood serum concentration of apoB produced according to the method of claim 1.

12. The test of claim 11 wherein the test is associated with instructions for obtaining the test spectral representation of the test blood serum sample, for application of the test.

13. The test of claim 12 wherein the instructions for obtaining the test spectral representation of the test blood serum sample, effectively reproduce the method of obtaining the mid infrared spectral representations for the blood serum samples from the set of standard blood serum samples to minimize any systematic error between the correlated spectral features of the test and those of the test spectral representation.

14. The test of claim 11 wherein the computer readable program instructions comprise program instructions for implementing the test of claim 10 to the test spectral representation.

15. The test of claim 14 wherein the computer readable program instructions further comprise program instructions for producing the test spectral representation from collected infrared light from the test blood serum sample.

16. The test of claim 15 wherein test is further associated with a spectrometer to be used for collecting the infrared light.

17. The test according to claim 11 wherein the test comprises a regression coefficient vector.

* * * * *